(12) United States Patent
Slone et al.

(10) Patent No.: US 6,306,463 B1
(45) Date of Patent: Oct. 23, 2001

(54) CITRIC ACID TRI-ALKYLAMIDE SURFACTANTS

(75) Inventors: Caroline Sassano Slone, Quakertown; Kevin Rodney Lassila, Macungie, both of PA (US); Ingrid Kristine Meier, Asbury, NJ (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/621,898

(22) Filed: Jul. 20, 2000

(51) Int. Cl.$^7$ ........................................................ B05D 3/02
(52) U.S. Cl. ........................ 427/384; 564/153; 564/159; 564/201; 252/356; 252/357
(58) Field of Search .............................. 427/384; 564/153, 564/157, 201; 252/356, 357

(56) References Cited

U.S. PATENT DOCUMENTS

| | | | |
|---|---|---|---|
| 3,946,074 | 3/1976 | Abramitits | 260/561 A |
| 5,273,684 | * 12/1993 | Traber et al. | 252/353 |
| 5,776,494 | 7/1998 | Guskey et al. | 424/484 |

FOREIGN PATENT DOCUMENTS

| | | |
|---|---|---|
| 944515 | 12/1963 | (GB) . |
| 06100833 | 4/1994 | (JP) . |
| 08302387A | 11/1996 | (JP) . |
| 0986768A | 11/1997 | (JP) . |

OTHER PUBLICATIONS

Medina, S. W., Sutovich, M. N., "Using Surfactants to Formulate VOC Compliant Waterbased Inks", Am. Ink Maker 1994, 72(2), 32–38.

Sheats, James R. and Smith, Bruce W., Microlithography, Science and Technology, MarcelDekker, Inc., 1998, pp 551–553.

Schwartz, Joel, "The Importance of Low Dynamic Surface Tension in Waterbone Coatings", Journal of Coatings Technology, Sep. 1992.

Wirth, Wolfgang, Storp, Siegfried and Jacobsen, Wolfgang, "Mechanisms Controlling Leaf Retention of Agricultural Spray Solutions", Pestic. Sci. 1991, 33, 411–420.

\* cited by examiner

*Primary Examiner*—Erma Cameron
(74) *Attorney, Agent, or Firm*—Michael Leach

(57) ABSTRACT

This invention provides water-based compositions which are essentially free of hydrocarbon solvents, particularly coating, ink, fountain solution, adhesive, agricultural and electronics cleaning compositions, manifesting reduced equilibrium and dynamic surface tension by the incorporation of a surface tension reducing amount of certain tri-alkylamides of citric acid of the structure

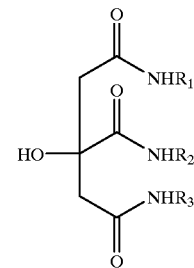

where $R_1$, $R_2$ and $R_3$ are independently C1 to C18 alkyl groups.

10 Claims, No Drawings

CITRIC ACID TRI-ALKYLAMIDE SURFACTANTS

FIELD OF THE INVENTION

The invention relates to the use of citric acid tri-alkylamides to reduce the surface tension in water-based systems.

BACKGROUND OF THE INVENTION

The ability to reduce the surface tension of water is of great importance in waterborne coatings, inks, adhesives, fountain solutions, agricultural formulations and cleaning compositions for electronics processes such as semiconductor manufacture because decreased surface tension translates to enhanced substrate wetting in actual formulations. Surface tension reduction in water-based systems is generally achieved through the addition of surfactants. Performance attributes resulting from the addition of surfactants include enhanced surface coverage, fewer defects, and a more uniform distribution. Equilibrium surface tension performance is important when a system is at rest. However, the ability to reduce surface tension under dynamic conditions is of great importance in applications where high surface creation rates are utilized. Such applications include the spraying, rolling and brushing of coatings or agricultural formulations, or high speed gravure or ink-jet printing. Dynamic surface tension is a fundamental quantity which provides a measure of the ability of a surfactant to reduce surface tension and provide wetting under high speed application conditions.

Traditional nonionic surfactants such as alkylphenol or alcohol ethoxylates and ethylene oxide (EO)/propylene oxide (PO) copolymers have excellent equilibrium surface tension performance but are generally characterized as having poor dynamic surface tension reduction. In contrast, anionic surfactants such as sodium dialkyl sulfosuccinates can provide good dynamic results, but are very foamy and impart water sensitivity to the finished coating.

In addition to the development of high-performance surfactants, there is considerable interest in the industry in surfactants with improved environmental characteristics. Environmental concerns have led to an increased use of environmentally compatible surfactants as alternatives have become available. In addition, the use of less favorable products, such as alkylphenol ethoxylate (APE) surfactants, has declined. This is, in part, due to the poor environmental characteristics of APE surfactants, such as incomplete biodegradation and a suspicion that they may function as endocrine mimics.

The demand for high-performance, eco-friendly surfactants has stimulated efforts in new surfactant development. From this work a new family of surfactants, referred to as alkyl polyglycoside (APG) surfactants, has emerged as a readily biodegradable, environmentally-friendly alternative to conventional surfactants. These materials, however, can be foamy and thus, are not suitable for a variety of coating, ink, adhesive and agricultural applications where the generation of foam is undesirable. Thus, not only is it desirable to obtain surfactants which exhibit excellent surface tension reducing capabilities, but it is also desirable that these surfactants exhibit low foam under dynamic application conditions and are environmentally friendly.

There is a need for surfactants which exhibit good equilibrium and dynamic surface tension properties, are low-foaming, and would be widely accepted in the waterborne coating, ink, adhesive, fountain solution, agricultural formulation and electronics manufacturing industries. Moreover, since there is substantial interest in the development of environmentally friendly surfactants, an essential attribute would be that these new surfactants not only possess the aforementioned desired performance attributes but also are derived from natural, renewable resources.

The importance of reducing equilibrium and dynamic surface tension in applications such as coatings, inks, adhesives, fountain solutions, agricultural formulations and electronics cleaning compositions, e.g., aqueous developer solutions for making semiconductor devices, is well-appreciated in the art.

Low dynamic surface tension is of great importance in the application of waterborne coatings. In an article, Schwartz, J. "The Importance of Low Dynamic Surface Tension in Waterborne Coatings", Journal of Coatings Technology, September 1992, there is a discussion of surface tension properties in waterborne coatings and a discussion of dynamic surface tension in such coatings. Equilibrium and dynamic surface tension were evaluated for several surface active agents. It is pointed out that low dynamic surface tension is an important factor in achieving superior film formation in waterborne coatings. Dynamic coating application methods require surfactants with low dynamic surface tensions in order to prevent defects such as retraction, craters and foam.

Efficient application of agricultural products is also highly dependent on the dynamic surface tension properties of the formulation. In an article, Wirth, W.; Storp, S.; Jacobsen, W. "Mechanisms Controlling Leaf Retention of Agricultural Spray Solutions"; Pestic. Sci. 1991, 33, 411–420, the relationship between the dynamic surface tension of agricultural formulations and the ability of these formulations to be retained on a leaf was studied. These workers observed a good correlation between retention values and dynamic surface tension, with more effective retention of formulations exhibiting low dynamic surface tension.

Low dynamic surface tension is also important in high-speed printing as discussed in the article "Using Surfactants to Formulate VOC Compliant Waterbased Inks", Medina, S. W.; Sutovich, M. N. Am. Ink Maker 1994, 72 (2), 32–38. In this article, it is stated that equilibrium surface tensions (ESTs) are pertinent only to ink systems at rest. EST values, however, are not good indicators of performance in the dynamic, high speed printing environment under which the ink is used. Dynamic surface tension is a more appropriate property. This dynamic measurement is an indicator of the ability of the surfactant to migrate to a newly created ink/substrate interface to provide wetting during high speed printing.

Tetramethylammonium hydroxide (TMAH) is the chemical of choice in aqueous alkaline solutions for developing photoresists according to Microlithography, Science and Technology, edited by J. R. Sheats and B. W. Smith, Marcel Dekker, Inc., 1998, pp 551–553. Surfactants are added to the aqueous TMAH solutions to reduce development time and scumming and to improve surface wetting.

U.S. Pat. No. 5,562,762 discloses an aqueous jet ink of water, dissolved dyes and a tertiary amine having two polyethoxylate substituents and that low dynamic surface tension is important in ink jet printing.

Citric acid (2-hydroxy-1,2,3-propanetricarboxylic acid) is found in nature and is a common metabolite for many plants and animals. It is classified as GRAS (Generally Recognized As Safe) by the U.S. Food and Drug Administration and is commonly used in foods, pharmaceuticals, detergents, cosmetics, cleaners and enhanced oil recovery. Citric acid is produced by the fermentation of sugars, such as corn starch or molasses.

Anionic surfactants based on citric acid amides are known.

JP 08302387A discloses the use of mono-amides prepared from citric acid and C10-C20 amines as surfactants in cosmetic formulations. These anionic surfactants are foamy and, thus, not suited for coating applications, such as the spraying, rolling and brushing of coatings or agricultural formulations, or high speed gravure or ink-jet printing.

U.S. Pat. No. 3 946 074 discloses di- and tri-amides of aliphatic polycarboxylic acids, including citric acid as growth regulators when applied to plants as an organic or aqueous solution or as an aqueous emulsion. The citramide, N,N,N',N'-tetramethyl-N"-1-methyldecyl citramide, was synthesized in Example 1. JP06100833 discloses aqueous ink compositions containing water soluble dyes or water dispersible pigments, a water soluble organic solvent and a tri-carboxylic acid amide.

GB 944515 discloses citric acid amides containing as part of the amide residue at least one residue of an alkylene diamine carrying on one nitrogen atom a C10–C22 aliphatic hydrocarbon residue. Citric acid amides of this type were shown to be active as bactericides and fungicides in aqueous compositions.

JP 09286768 discloses tri-amides of citric acid containing C8–C22 alkyl or alkylene groups, e.g., trioctyl- and tridodecylamides of citric acid, as lubricants, releases and dispersants for the processing of thermoplastic and thermosetting resins and synthetic rubber. In all examples, the citramide additive was added to non-aqueous compositions.

U.S. Pat. No. 5 776 494 discloses the use of alkylamides of di-and/or tribasic carboxylic acids, e.g., 2-hydroxy-1,2,3-propanetributylamide, as gelling agents in pharmaceutical compositions in the form of a gel or gel stick. The compositions are prepared using an anhydrous liquid carrier which contains <5% water.

SUMMARY OF THE INVENTION

The invention provides water-based compositions which contain an organic or inorganic compound, particularly aqueous organic protective or decorative coating, ink, adhesive, fountain solution, agricultural and electronics cleaning compositions, having reduced equilibrium and dynamic surface tension by incorporation of an effective amount of a tri-alkylamide of citric acid ("citramide") of the formula:

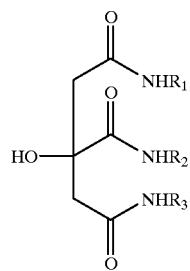

where $R_1$, $R_2$ and $R_3$ are independently C1 to C18 alkyl groups. It is desirable that an aqueous solution of the citramide demonstrates a dynamic surface tension of less than 50 dynes/cm at a concentration of $\leq$5 wt % in water at 25° C. and 20 bubble/second according to the maximum bubble pressure method. The maximum bubble pressure method of measuring surface tension is described in *Langmuir* 1986, 2, 428–432, which is incorporated by reference.

By "water-based", "aqueous" or "aqueous medium", we mean, for purposes of this invention, a solvent or liquid dispersing medium which comprises at least 90 wt %, preferably at least 95 wt %, water. Obviously, an all water medium is also included. In addition, it is desirable that the water-based compositions are essentially free of hydrocarbon solvent.

Also provided is a method for lowering the equilibrium and dynamic surface tension of such aqueous compositions by the incorporation of these citramide compounds.

Also provided is a method for applying a coating of a water-based inorganic or organic compound-containing composition to a surface to partially or fully coat the surface with the water-based composition and drying the composition to deposit a coating, the composition containing an effective amount of a citramide compound of the above structure for reducing the dynamic surface tension of the water-based composition.

There are significant advantages associated with the use of these citramides in water-based organic coatings, inks, adhesives, fountain solutions, agricultural and electronics chemical compositions and these advantages include:

water-borne coatings, inks, adhesives, fountain solutions, agricultural and electronics chemical formulations which may be applied to a variety of substrates with excellent wetting of substrate surfaces;

a reduction in coating or printing defects such as orange peel and flow/leveling deficiencies;

coating and ink compositions capable of high speed application;

low-foam surfactants capable of reducing dynamic surface tension;

low-foam surfactants which have low odor;

water-borne compositions using a surfactant derived from natural, renewable resources, thus making such formulations environmentally favorable; and an ability to formulate low surface tension aqueous electronics cleaning and processing solutions, including photoresist developer solutions, for the semiconductor manufacturing industry with good wetting and extremely low foam.

Because of their excellent surfactant properties and the ability to control foam, these materials are likely to find use in many applications in which reduction in dynamic and equilibrium surface tension and low foam are important. Applications in which low foam is important include various wet-processing textile operations, such as dyeing of fibers, fiber scouring, and kier boiling, where low-foaming properties would be particularly advantageous; they may also have applicability in soaps, water-based perfumes, shampoos, detergents, cleaners, cosmetics and food processing where their marked ability to lower surface tension while simultaneously producing substantially no foam would be highly desirable.

In addition, the demands of the semiconductor fabrication industry have led to the requirement for high performance surfactants and wetting agents for photoresist developer formulations. As line features shrink to smaller sizes and photoresist substrate materials become more aliphatic in nature (i.e., lower surface energy), aqueous developer solutions increasingly are being formulated with surface tension reducing agents.

An additional requirement for these developers, accentuated by the move toward larger wafer sizes, is that they exhibit low foam. This is particularly important when the so-called spray puddle techniques are used in applying the developer solution, wherein the developer is sprayed over increasingly larger areas. Even in cases where puddle or immersion techniques are used, microbubble entrainment during spreading of the solution over the photoresist surface can lead to defects. The materials according to the present invention give efficient reduction of surface tension of aqueous developer solutions and exceedingly low foam, even under extreme conditions. Other applications in the electronics industry using aqueous processing media would also benefit from good dynamic wetting and low foam.

DETAILED DESCRIPTION OF THE INVENTION

This invention relates to the use of citramide compounds of the structure

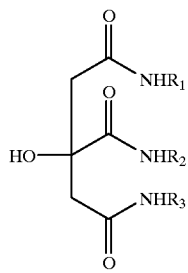

where $R_1$, $R_2$ and $R_3$ are C1 to C18 alkyl groups, preferably C2 to C8 and most preferably C3 to C5, for the reduction of equilibrium and dynamic surface tension in water-based compositions which are essentially free of aliphatic and aromatic hydrocarbon solvents and contain an organic compound, particularly protective or decorative coating, ink, fountain solution, adhesive, agricultural and electronics processing compositions containing organic compounds such as polymeric resins, organic bases, herbicides, fungicides, insecticides or plant growth modifying agents. It is desirable that an aqueous solution of the citramide demonstrates a dynamic surface tension of less than 50 dynes/cm at a concentration of $\leq 5$ wt % in water at 25° C. and 20 bubble/second according to the maximum-bubble-pressure method.

In one aspect of the invention the citramides of the above formula display excellent ability to reduce equilibrium and dynamic surface tension while producing substantially no foam.

These materials may be prepared by the reaction of primary amines with citric acid or citric acid esters. The reaction is illustrated below:

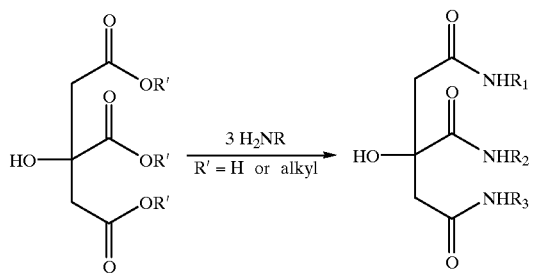

The animation reaction to form the amide may be performed using a variety of conditions well known in the organic chemical art as described in the *Kirk-Othmer Encyclopedia of Chemical Technology*, 4th Ed., Vol. 2, p. 348–351. The preferred method involves the reaction of a citric acid ester with 3 or more equivalents of amine in a protic solvent.

All primary amines or mixtures of primary amines containing the requisite C1 to C18 alkyl substituents may be utilized for the preparation of the tri-alkylcitramides of this invention, with amines containing 2–8 carbons being preferred and those containing 3–5 carbons being especially preferred. It is preferred that the tri-alkylcitramides contain a total of 8–20 amide alkyl carbons and those containing a total of 9–15 amide alkyl carbons are especially preferred. Alkyl groups which are suitable should have sufficient carbon atoms to confer surface activity (i.e. an ability to reduce the surface tension of water) to the material but not enough carbon atoms to decrease the solubility to the extent that the ability of the material to reduce surface tension is insufficient for a particular application. In general, an increase in the carbon number increases the efficiency of the resulting tri-alkylcitramide (i.e. less surfactant is required to obtain a given decrease in surface tension), but it decreases the surfactant's ability to reduce surface tension at high surface creation rates. The latter effect is a result of the fact that increased carbon number generally decreases the water solubility of the material, and consequently, diminishes the diffusive flux of surfactant to newly-created surfaces. Generally, in the practice of this invention, it is desirable to choose amide alkyl groups such that the resulting tri-alkylcitramides have a solubility limit in water of $\leq 10$ wt % and preferably from 0.1 to 0.5 wt %.

The alkyl groups in the citramides may be the same or different and may be linear or branched. Examples of suitable alkyl groups are methyl, ethyl, n-propyl, iso-propyl, n-butyl, iso-butyl, sec-butyl, n-pentyl, 2-pentyl, 3-pentyl, iso-pentyl, neopentyl, cyclopentyl, 2-methylbutyl, 3-methyl-2-butyl, n-hexyl, 2-hexyl, 3-hexyl, cyclohexyl, 2-ethylbutyl, 4-methyl-2-pentyl, n-heptyl, n-octyl, n-2-ethylhexyl, n-nonyl, n-decyl, n-undecyl, n-dodecyl and so on. Of these derivatives those which contain a total of 8 to 20 amide alkyl carbons are preferred and those containing 9 to 15 alkyl carbons especially preferred, with those containing 12 alkyl carbons being the most preferred, especially in the case where $R_1=R_2=R_3$=butyl.

An amount of tri-alkylcitramide that is effective to reduce the equilibrium and/or dynamic surface tension of the water-based, organic compound-containing composition may range from 0.001 to 20 wt %, preferably 0.01 to 10 wt %, of the aqueous composition. Naturally, the most effective amount will depend on the particular application and the solubility of the citramide.

The citramides are suitable for use in an aqueous composition comprising in water an inorganic compound which is, for example, a mineral ore or a pigment or an organic compound which is a pigment, a polymerizable monomer, such as addition, condensation and vinyl monomers, an oligomeric resin, a polymeric resin, a detergent, a cleaning agent, a dissolution agent such as trimethylammonium hydroxide (TMAH), a herbicide, a fungicide, an insecticide, or a plant growth modifying agent.

In the following water-based organic coating, ink, adhesive, fountain solution, agricultural and photoresist developer compositions containing a tri-alkylcitramide according to the invention, the other listed components of such compositions are those materials well known to the workers in the relevant art.

A typical water-based protective or decorative organic coating composition to which the tri-alkylcitramide surfactants of the invention may be added would comprise in an aqueous medium 30 to 80 wt % of a coating composition containing the following components:

| Water-Based Organic Coating Composition | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvent |
| 0.01 to 10 wt % | Surfactant/Wetting Agent/Flow and Leveling Agents |
| 0.01 to 5 wt % | Tri-alkylcitramide |

A typical water-based ink composition to which the citramide surfactants of the invention may be added would comprise in an aqueous medium 20 to 60 wt % of an ink composition containing the following components:

| Water-Based Ink Composition | |
|---|---|
| 1 to 50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-Borne/Water-Dispersible/Water-Soluble Resins |
| 0 to 30 wt % | Coalescing or Other Solvent |
| 0.01 to 10 wt % | Surfactant/Wetting Agent |
| 0.01 to 10 wt % | Processing Aids/Defoamers/Solubilizing Agents |
| 0.01 to 5 wt % | Tri-alkylcitramide |

A typical water-based agricultural composition to which the citramide surfactants of the invention may be added would comprise in an aqueous medium 0.1 to 80 wt % of an agricultural composition containing the following components:

| Water-Based Agricultural Composition | |
|---|---|
| 0.1 to 50 wt % | Pesticide, Insecticide, Herbicide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.01 to 50 wt % | Tri-alkylcitramide |

A typical water-based fountain solution composition containing the citramide surfactants of the invention would comprise the following components:

| Water-Based Fountain Solution | |
|---|---|
| 0.05 to 10 wt % | Film formable, water soluble macromolecule |
| 1 to 25 wt % | Alcohol, glycol, or polyol with 2–12 carbon atoms, water soluble or can be made to be water soluble |
| 0.01 to 20 wt % | Water soluble organic acid, inorganic acid, or a salt thereof |
| 30 to 70 wt % | Water |
| 0.01 to 5 wt % | Tri-alkylcitramide |

A typical water-based adhesive composition to which the tri-alkylcitramide surfactants of the invention may be added would comprise in an aqueous medium 30 to 65 wt % of an adhesive composition containing the following components:

| Water-Based Adhesive | |
|---|---|
| 50 to 99 wt % | Polymeric Resin (SBR, VAE, Acrylic) |
| 0 to 50 wt % | Tackifier |
| 0 to 0.5 wt % | Defoamer |
| 0.5 to 2 wt % | Tri-alkylcitramide |

A typical water-based photoresist developer, or electronic cleaning, composition to which the tri-alkylcitramide surfactants of the invention may be added would comprise an aqueous medium containing the following components:

| Water-Based Photoresist Developer Composition | |
|---|---|
| 0.1 to 3 wt % | Tetramethylammonium Hydroxide |
| 0 to 4 wt % | Phenolic Compound |
| 10 to 10,000 ppm | Tri-alkylcitramide |

The following Examples 1–4 illustrate the synthesis of various citric acid tri-alkylamides. All tri-alkylcitramides were synthesized and characterized via a combination of Gas Chromatography (GC) and Gas Chromatography/Mass Spectrometry (GCIMS) or Nuclear Magnetic Resonance (NMR) spectroscopy. All citramides prepared ranged from 80% to >99% pure.

EXAMPLE 1

N,N',N"-tri-n-propylcitramide was prepared by the reaction of n-propylamine with triethylcitrate. To a round-bottomed flask were added triethylcitrate (30.245 g; 1 eq), n-propylamine (19.427 g; 3.16 eq) and methanol (40 mL). The clear light yellow solution stirred for 3 days at room temperature prior to the removal of methanol via rotary evaporation at 50° C. The resulting yellow liquid was dried in vacuo at 70° C. and a tacky white solid was obtained. The crude solid was triturated using diethylether, collected via filtration and dried in vacuo to give a white powder with a slight odor (19.19 g; 55% yield).

EXAMPLE 2

N,N',N"-tri-n-butylcitramide was prepared by the reaction of n-butylamine with triethylcitrate. To a round-bottomed flask were added triethylcitrate (31.485 g; 0.1140 mole, 1 eq) and methanol (40 mL). To this solution, n-butylamine (24.999 g; 3.00 eq) was slowly poured. The clear light yellow solution stirred for 3 days at room temperature prior to the removal of methanol via rotary evaporation at 60° C. The resulting crude tacky solid was triturated using diethylether, collected via filtration and dried in vacuo to give a white powder with a slight amine odor (23.95 g; 58% yield).

EXAMPLE 3

N,N',N"-tri-iso-butylcitramide was prepared by the reaction of iso-butylamine with triethylcitrate. To a round-bottomed flask were added triethylcitrate (30.001 g; 1 eq), iso-butylamine (24.034 g; 3.03 eq) and methanol (40 mL). The clear light yellow solution stirred for 2 days at room temperature and then additional isobutylamine (3.06 eq) was added. After stirring overnight, a wet white solid was observed. Methanol was removed in vacuo and the solid was triturated using diethylether, collected via filtration and dried in vacuo to give a white powder with no detectable odor (31.09 g; 80.3% yield).

EXAMPLE 4

N,N',N"-tri-iso-amylcitramide was prepared by the reaction of iso-amylamine with triethylcitrate. To a round-bottomed flask were added triethylcitrate (30.001 g, 1 eq), iso-amylamine (28.399 g, 3.0 eq) and methanol (40 mL). The clear light yellow solution stirred for 2 days at room temperature and then additional amine (1.1 eq) was added. After stirring 1 week, a clear yellow solution was observed. Methanol was removed in vacuo and the resulting white solid was triturated using diethylether, collected via filtration and dried in vacuo to give a white powder with a very slight odor (22.52 g, 52.1% yield).

EXAMPLES 5–8

Solutions of the citramides of Examples 1–4 in distilled water were prepared. Dynamic surface tension data were obtained using the maximum-bubble pressure method at bubble rates from 0.1 bubbles/second (b/s) to 20 b/s as described in *Langmuir* 1986, 2, 428–432. These data provide information about the performance of a surfactant at conditions from near-equilibrium (0.1 b/s) through extremely high surface creation rates (20 b/s). In practical terms, high bubble rates correspond to high printing speeds in lithographic printing, high spray or roller velocities in coating applications, rapid application rates for agricultural products and electronics cleaning and processing.

The dynamic surface tension data and solubility limits are provided in Table 1. The solubility limits of Examples 6 and 7 were determined by intersection of the linear portion of a surface tension/ln (concentration) curve with the limiting surface tension as is described in many textbooks. Since Example 8 contained insoluble material at 0.005 wt %, the solubility limit is reported as <0.005 wt %. Also, the solubility limit of ~10 wt % reported for Example 1 is the lowest concentration at which a significant amount of insoluble material was seen. The relative efficiency of surfactants can be obtained by comparing surface tension reduction of solutions containing the same amount of different surfactants. Such data is given for 0.1 wt %, solutions of the tri-alkylcitramides at 1.0 and 6.0 b/s. The limiting surface tensions at 0.1, 1, 6 and 20 b/s represent the lowest surface tensions in water which can be achieved at the given surface creation rates for a given surfactant regardless of the amount of surfactant used and is used to evaluate the effectiveness of a surfactant. These values give information about the relative ability of a surfactant to reduce surface defects under near-equilibrium conditions (0.1 b/s) through very dynamic conditions (20 b/s). Lower surface tensions would allow the elimination of defects upon application of a formulation onto lower energy surfaces.

TABLE 1

Surface Tension Data for Tri-alkylcitramide Surfactants

| Structure | solubility limit[a] | γ limiting[b] | | | | γ (0.1 wt % solution)[b] | |
|---|---|---|---|---|---|---|---|
| | | (0.1 b/s) | (1 b/s) | (6 b/s) | (20 b/s) | (1 b/s) | (6 b/s) |
| Example 5 (Example 1) | ~10 | 42.9 | 43.1 | 43.7 | 44.9 | 66.7 | 67.2 |
| Example 6 (Example 2) | 0.4 | 43.6 | 43.9 | 44.6 | 46.2 | 51.2 | 52.6 |
| Example 7 (Example 3) | 0.2 | 46.6 | 46.8 | 47.3 | 48.4 | 51.8 | 52.5 |

TABLE 1-continued

Surface Tension Data for Tri-alkylcitramide Surfactants

| Structure | solubility limit[a] | γ limiting[b] | | | | γ (0.1 wt % solution)[b] | |
| --- | --- | --- | --- | --- | --- | --- | --- |
| | | (0.1 b/s) | (1 b/s) | (6 b/s) | (20 b/s) | (1 b/s) | (6 b/s) |
| Example 8 (Example 4) | <0.005 | 51.6[c] | 62.6[c] | 67.0[c] | 71.4[c] | 63.3 | 66.6 |

[a]Weight %
[b]Dyne/cm
[c]Limiting γ at 0.005 wt. % surfactant.

When the triisoamylamide (Ex 4) used in Example 8 was added to water at 5 wt %, a considerable amount of material remained undissolved. Measuring the dynamic surface tension of this aqueous mixture gave the following y values: 45.7 dyne/cm (0.1 b/s), 45.9 dyne/cm (1 b/s), 46.4 dyne/cm (6 b/s) and 47.4 dyne/cm (20 b/s).

The data in Table 1 illustrate that the tri-alkylcitramides have the ability to reduce the dynamic surface tension of an aqueous composition and that in the majority of cases low surface tension can be maintained even under conditions in which surface is created at a rapid rate (i.e. 20 b/s). Examples 5–8 demonstrate that tri-alkylcitramides containing 9 to 15 carbon atoms exhibit surface tension values of less than 48 dyne/cm at a concentration of <10 wt % in water at 25° C. and at 0.1 b/s. Furthermore, tri-alkyl-citramides containing 12 carbon atoms demonstrate a reduction in the dynamic surface tension of aqueous solutions to less than 50 dyne/cm under very dynamic conditions (20 b/s) and at a concentration of ≦0.5 wt % in water at 25° C. In comparison, tri-alkyl-citramides containing 9 carbon atoms require a much larger amount of sample to achieve similar dynamic surface tension reduction. Surprisingly, tri-alkylcitramides which contain C4 groups exhibit an optimum combination of effectiveness and efficiency in regard to surface tension reduction of aqueous compositions.

Alkyl group branching was not found to result in improved performance. In comparison to N,N',N"-tri-iso-butylcitramide, N,N',N"-tri-n-butylcitramide was more soluble and thus, more effective reducing the dynamic surface tension of water. Therefore, of the tri-alkylcitramides which contain linear alkyl chains are preferred for the reduction of surface tension of water in water-based, organic compound containing compositions, including waterborne coatings, inks, adhesives, fountain solutions, agricultural formulations and electronics cleaning compositions. However, ultimately the choice of tri-alkylcitramide will depend upon the application.

EXAMPLES 9–13

The foaming properties of a 0.1 wt % solutions of the tri-alkylcitramides (N,N',N"-tri-n-propylcitramide, N,N',N"-tri-n-butylcitramide, N,N',N"-tri-iso-butylcitramide and N,N',N"-tri-iso-amylcitramide) were examined using a procedure based upon ASTM D 1173-53. In this test, a 0.1 wt % solution of the citramide surfactant was added from an elevated glass pipette to a receiver containing the same solution. The foam height was measured at the completion of the addition ("Initial Foam Height") and the time required for the foam to dissipate at the air-liquid interface ("Time to 0 Foam") was recorded. This test provided a comparison between the foaming characteristics of the various citramides. In general, in coatings, inks, adhesives, agricultural and electronics cleaning formulations, foam is undesirable because it complicates handling and can lead to coating and print defects, and to inefficient application of materials. The results for the tri-alkylcitramides prepared in Examples 1–4 are reported in Table 2.

TABLE 2

Foam Test Data

| Structure | initial foam (cm) | time to zero foam |
| --- | --- | --- |
| Example 9 (Example 1) | 2.8 | 10 sec |
| Example 10 (Example 2) | 1.3 | 9 sec |

TABLE 2-continued

Foam Test Data

| Structure | initial foam (cm) | time to zero foam |
|---|---|---|
| Example 12 (Example 3) | 1.0 | 10 sec |
| Example 13 (Example 4) | 1.3 | 2 sec |

A drawback to the use of many conventional surfactants in coatings, inks, adhesives, agricultural, electronic chemical and cleaning formulations is the formation of considerable quantities of long-lasting foam in these systems. For such applications, it is desired that a surfactant form as little foam as possible and that the foam which forms dissipates quickly. The data in Table 2 show that the compounds of this invention formed very little initial foam and that the foam which formed dissipated quickly. Therefore, in addition to their ability to reduce the surface tension of organic-containing aqueous compositions under both equilibrium and dynamic conditions, tri-alkylcitramide surfactants have desirable foam properties with respect to their use in coatings, inks, adhesives, agricultural and electronics cleaning formulations.

STATEMENT OF INDUSTRIAL APPLICATION

The invention provides compositions suitable for reducing the equilibrium and dynamic surface tension in water-based coating, ink, adhesive, fountain solution, agricultural and electronics cleaning compositions.

We claim:

1. In a method for applying a coating of a water-based composition to a surface to partially or fully coat the surface and drying the coating, the composition containing an inorganic or organic compound and an effective amount of a surfactant for reducing the dynamic surface tension of the composition, the improvement which comprises employing as the surfactant a tri-alkylamide of citric acid of the formula:

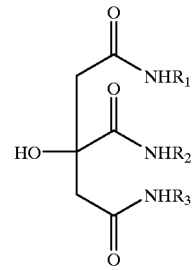

where $R_1$, $R_2$ and $R_3$ are independently C1 to C18 alkyl groups.

2. The method of claim 1 in which the water-based composition is selected from the group consisting of aqueous organic protective or decorative coating, ink, adhesive, fountain solution, agricultural, photoresist developing and electronics cleaning compositions and the tri-alkylamide is present at 0.001 to 20 wt % of the water-based composition.

3. The method of claim 2 in which an aqueous solution of the tri-alkylamide of citric acid demonstrates a dynamic surface tension of less than 50 dynes/cm at a concentration of $\leq 5$ wt % in water at 25° C. and 20 bubbles/second according to the maximum-bubble-pressure method.

4. The method of claim 1 in which $R_1$, $R_2$ and $R_3$ are C2 to C8 alkyl groups.

5. The method of claim 1 in which $R_1$, $R_2$ and $R_3$ are C3 to C5 alkyl groups.

6. The method of claim 1 in which $R_1$, $R_2$ and $R_3$ are the same.

7. The method of claim 6 in which $R_1$, $R_2$ and $R_3$ are a C4 alkyl group.

8. The method of claim 6 in which $R_1$, $R_2$ and $R_3$ are a C5 alkyl group.

9. The method of claim 6 in which the alkyl groups are n-butyl.

10. The method of claim 6 in which the alkyl groups are iso-butyl.

* * * * *